(12) United States Patent
Kautzsch (10) Patent No.: US 10,270,002 B2
(45) Date of Patent: Apr. 23, 2019

(54) INTEGRATED LIGHT EMITTING DEVICE, INTEGRATED SENSOR DEVICE, AND MANUFACTURING METHOD

(71) Applicant: Infineon Technologies Dresden GmbH, Dresden (DE)

(72) Inventor: Thoralf Kautzsch, Dresden (DE)

(73) Assignee: Infineon Technologies Dresden GmbH, Dresden (DE)

( * ) Notice: Subject to any disclaimer, the term of this patent is extended or adjusted under 35 U.S.C. 154(b) by 153 days.

(21) Appl. No.: 15/196,203

(22) Filed: Jun. 29, 2016

(65) Prior Publication Data
US 2017/0005220 A1 Jan. 5, 2017

(30) Foreign Application Priority Data
Jun. 30, 2015 (DE) .................. 10 2015 110 496

(51) Int. Cl.
| | |
|---|---|
| *H01L 31/173* | (2006.01) |
| *G01N 21/552* | (2014.01) |
| *H01L 33/00* | (2010.01) |
| *H01L 33/20* | (2010.01) |
| *G02B 6/12* | (2006.01) |

(52) U.S. Cl.
CPC ......... *H01L 31/173* (2013.01); *G01N 21/552* (2013.01); *G02B 6/12004* (2013.01); *H01L 33/005* (2013.01); *H01L 33/20* (2013.01)

(58) Field of Classification Search
CPC ..... H01L 31/173; H01L 33/005; H01L 33/20; G02B 6/12004
See application file for complete search history.

(56) References Cited

U.S. PATENT DOCUMENTS

| | | | |
|---|---|---|---|
| 5,428,227 A | 6/1995 | Satoh | |
| 5,631,474 A | 5/1997 | Saitoh | |
| 7,408,203 B2 | 8/2008 | Kim et al. | |
| 7,599,277 B1 * | 10/2009 | Kato | ............ G11B 7/124 369/112.09 |
| 7,709,795 B2 | 5/2010 | Yamanaka et al. | |
| 2002/0105809 A1 * | 8/2002 | Kuijk | ............ H01L 27/153 362/301 |

(Continued)

FOREIGN PATENT DOCUMENTS

| | | |
|---|---|---|
| CN | 1684281 A | 10/2005 |
| CN | 101248337 A | 8/2008 |

(Continued)

OTHER PUBLICATIONS

Schell, Mike and Dan Int-Haut, "Demand Control Ventilation Using CO2", ASHRAE Journal (Feb. 2001), pp. 1-6.

(Continued)

*Primary Examiner* — Joseph Galvin, III
(74) *Attorney, Agent, or Firm* — Volpe and Koenig, P.C.

(57) ABSTRACT

The present disclosure relates to an integrated light emitting device. The integrated light emitting device comprises a substrate of semiconductor material, a light emitting unit integrated into the semiconductor material, and at least one cavity formed into the semiconductor material between the substrate and the light emitting unit. At least portions of the at least one cavity may be formed by Silicon-On-Nothing (SON) process steps.

20 Claims, 9 Drawing Sheets

(56) References Cited

U.S. PATENT DOCUMENTS

| | | | | |
|---|---|---|---|---|
| 2003/0007736 | A1* | 1/2003 | Harada | G02B 6/12004 385/49 |
| 2004/0105476 | A1 | 6/2004 | Wasserbauer | |
| 2006/0033126 | A1* | 2/2006 | Mouli | H01L 27/14621 257/227 |
| 2009/0068668 | A1 | 3/2009 | Duer | |
| 2009/0312200 | A1 | 12/2009 | Pompa | |
| 2010/0006784 | A1 | 1/2010 | Mack et al. | |
| 2011/0248302 | A1* | 10/2011 | Choi | H01L 27/15 257/98 |
| 2014/0003457 | A1 | 1/2014 | Shastri et al. | |
| 2014/0061677 | A1* | 3/2014 | Jakoby | G01N 21/552 257/80 |
| 2014/0231635 | A1* | 8/2014 | Kerness | G01S 17/026 250/226 |
| 2015/0171262 | A1* | 6/2015 | Kim | H01L 33/32 257/13 |
| 2016/0087404 | A1* | 3/2016 | Lell | H01S 5/0078 372/44.01 |

FOREIGN PATENT DOCUMENTS

| | | |
|---|---|---|
| WO | 2001097294 A2 | 12/2001 |
| WO | 2007081549 A2 | 7/2007 |
| WO | 2010008119 A1 | 1/2010 |

OTHER PUBLICATIONS

Sauer, M., U. Schiller, M. Arndt and M. Wolz, "A Climate Control Sensor for Optimizing the Circulating-Air Mode by Controlling the CO2 Level Inside the Passenger Compartment", Robert Bosch GmbH, 05A9023, no date, pp. 1-7.

Zosel, J., W. Oelssner, M. Decker, G. Gerlach and U. Guth, "The Measurement of Dissolved and Gaseous Carbon Dioxide Concentration", IOP Publishing, Meas. Sci. Technol. 22 (May 20, 2011) 072001, pp. 1-45. doi: 10.1088/0957-0233/22/7/072001.

Hodgkinson, Jane, Richard Smith, Wah On Ho, John R. Saffell and Ralph P. Tatam, "Non-dispersive Infra-red (NDIR) Measurement of Carbon Dioxide at 4.2μm in a Compact and Optically Efficient Sensor", Sensors and Actuators B: Chemical, vol. 186, Sep. 2013, pp. 580-588.

Ma, Hongyu, Wenjuan Wang and Xiaowen Liu, Methane Detection With High Temperature All-silicon Microheater, IEEE SENSORS 2014 Proceedings, Nov. 2-5, 2014 pp. 186-189. doi 10.1109/ICSENS.2014.6984964.

Mastrangelo, C.H. and R.S. Muller, "Vacuum-Sealed Silicon Micromachined Incandescent Light Source", IEEE Electron Devices Meeting, 1989, IEDM '89 Technical Digest, pp. 503-506. doi: 10.1109/IEDM.1989.74331.

de Souza, Michelly, Bertrand Rue, Denis Flandre and Marcelo A. Pavanello, "Thin-Film Lateral SOI PIN Diodes for Thermal Sensing Reaching the Cryogenic Regime", Journal Integrated Circuits and Systems 2010, vol. 5, No. 2, pp. 160-167.

Harken, F., E. Vetsch, D. Meschede, M. Sokolowski, and A. Rauschenbeutel, Ultra-sensitive Surface Absorption Spectroscopy Using Sub-Wavelength Diameter Optical Fibers, Optics Express, Sep. 17, 2007 vol. 15, No. 19, pp. 11952-11958. doi: 10.1364/OE.15.11952.

Rauschenbeutel, Von Arno, "Glasfasem dunner als Licht", Forschungsmagazin, Jan. 2009 pp. 19-21.

Voros, Zoltan and Rainer Johnsen, "A Simple Demonstration of Frustrated Total Internal Reflection", Am. J. Phys. 76(8), Aug. 2008, pp. 746-749.

* cited by examiner

PRIOR ART

INTEGRATED LIGHT EMITTING DEVICE, INTEGRATED SENSOR DEVICE, AND MANUFACTURING METHOD

FIELD

Embodiments generally relate to semiconductor devices and methods for manufacturing semiconductor devices, and, more particularly, to integrated light emitting devices and related integrated sensor devices

BACKGROUND

Electronic sensors generally measure a physical quantity and convert the measured physical quantity into a signal that is provided to an electronic instrument (e.g., integrated chip processor). In recent years, the number of areas using sensors has vastly expanded. For example, sensors can be found in diverse applications such as chemical agent detection units, medical diagnostic equipment, industrial process controls, pollution monitoring, automobiles, etc.

Infrared sensors such as for instance mid-infrared (MIR) sensors measure radiation emitted in the infrared (IR) portion of the electro-magnetic spectrum from objects having a temperature above absolute zero. The mid-infrared spectrum covers electromagnetic radiation with wavelengths in a range of approximately 2-25 µm. By measuring changes in the MIR spectrum, sensors are able to measure changes in a sample's chemistry or temperature, for example.

The reduction of the optical path length (millimeter and centimeter-range today) is one central tasks on the way to monolithically integrated IR sensors. One promising approach is the application of evanescent surface fields in waveguides of sub-wavelength diameters. To take full advantage of this concept, an efficient collimation and coupling of infrared light into a fiber as well as an excellent thermal isolation of a light emitter is desired.

SUMMARY

An embodiment of the present disclosure relates to a semiconductor-based integrated light emitting device. The device comprises a substrate comprising a semiconductor material, i.e., a semiconductor substrate. The integrated device further comprises a light emitting unit integrated into the semiconductor material, and at least one cavity formed into the semiconductor material between the substrate and the light emitting unit.

In particular, at least parts of the cavity may be formed below portions of the light emitting unit and above portions of the semiconductor substrate. Commonly, such a cavity is referred to as Silicon-On-Nothing (SON) cavity.

In some embodiments, the light emitting unit comprises, as light source, an electrically conductive structure formed in the semiconductor material. The electrically conductive structure is configured to emit light when a supply voltage is applied to terminals of the electrically conductive structure.

In some embodiments, the electrically conductive structure comprises crystalline, polycrystalline or amorphous semiconductor material.

In some embodiments, the electrically conductive structure comprises an electrically conductive filament extending perpendicular to a direction of a light beam emitted from the light emitting unit.

In some embodiments, the light emitting unit further comprises a beam shaping portion which is configured to collimate light emitted from the electrically conductive structure. The beam shaping portion may comprise a light-reflecting rounded or parabolic edge of the light emitting unit's semiconductor material.

In some embodiments, the electrically conductive structure substantially extends through a focus of the rounded or parabolic edge.

In some embodiments, the light emitting unit further comprises a filter portion formed in the semiconductor material. The filter portion may be configured to have at least one pass band in the spectral infrared region.

In some embodiments, the filter portion comprises one or more trenches formed into the light emitting unit's semiconductor material.

In some embodiments, the light emitting unit is arranged in a portion of the semiconductor material sealed off an environment. The light emitting unit in the sealed portion may be at least partially surrounded by an evacuated cavity.

In some embodiments, the integrated light emitting device further comprises a sealing layer formed above the light emitting unit and at least one cavity between the light emitting unit and the sealing layer.

In some embodiments, the integrated light emitting device further comprises a waveguide coupled to a light outlet of the light emitting unit. The waveguide may be configured to provide interaction between guided light and a measurement medium surrounding the waveguide.

In some embodiments, the waveguide and the light emitting unit are integrally formed into the semiconductor material.

In some embodiments, the waveguide is arranged in a portion of the semiconductor material open to an environment. The light emitting unit may be arranged in a portion of the semiconductor material sealed off the environment.

In some embodiments, a width of the waveguide is smaller than the emitted light's wavelength. Optionally, a height of the waveguide may be larger than the light's wavelength.

According to a further aspect of the present disclosure it is provided an integrated sensor device. The integrated sensor device comprises a semiconductor substrate, a light emitting unit formed into the semiconductor substrate, a light detecting unit formed into the semiconductor substrate, and a waveguide formed into the semiconductor substrate between the light emitting unit and the light detecting unit. The waveguide is formed in a portion of the semiconductor substrate open to an environment to provide interaction between guided light and a measurement medium surrounding the waveguide. The light emitting unit is formed in a portion of the semiconductor substrate sealed off the environment. Further, the light emitting unit in the sealed portion is at least partially surrounded by an evacuated cavity.

In particular, at least parts of the evacuated cavity may be formed below portions of the light emitting unit and above portions of the semiconductor substrate. Commonly, such a cavity is referred to a Silicon-On-Nothing (SON) cavity.

According to a further aspect of the present disclosure it is provided a method for forming an integrated light emitting device. The method includes integrating a light emitting unit into a semiconductor material of a semiconductor substrate and forming at least one cavity into the semiconductor material between the semiconductor substrate and the light emitting unit. Note that the at least one cavity may actually be formed into the semiconductor material before the light emitting unit is created.

In some embodiments, forming the at least one cavity comprises forming a cavity below the light emitting unit by using a Silicon-On-Nothing (SON) processing sequence.

In some embodiments, integrating the light emitting unit comprises integrally forming, with the light emitting unit, a waveguide into the semiconductor material.

In some embodiments, integrating the light emitting unit comprises forming an electrically conductive filament structure into the integrating the light emitting unit.

In some embodiments, integrating the light emitting unit comprises forming a filter structure having one or more trenches into the semiconductor material.

In some embodiments, integrating the light emitting unit comprises forming a light-reflecting curved or parabolic edge into the light emitting unit's semiconductor material, the curved or parabolic edge acting as beam shaping element.

Embodiments may combine an integrated light emitter, a collimation unit and a spectral filter on a single semiconductor element. This element may be thermally isolated from surrounding material by evacuated cavities. Thereby efficient collimation and coupling of infrared (IR) light into an optical sub-wavelength fiber as well as an excellent thermal isolation of the emitter may be provided.

BRIEF DESCRIPTION OF THE DRAWINGS

Some embodiments of apparatuses and/or methods will be described in the following by way of example only, and with reference to the accompanying figures, in which.

DETAILED DESCRIPTION

Various example embodiments will now be described more fully with reference to the accompanying drawings in which some example embodiments are illustrated. In the figures, the thicknesses of lines, layers and/or regions may be exaggerated for clarity.

Accordingly, while further embodiments are capable of various modifications and alternative forms, some example embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like or similar elements throughout the description of the figures.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of further example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art, unless expressly defined otherwise herein.

A constantly increasing amount of publications and concepts deals with detection and characterization of chemicals in gases and other fluids. The progressive miniaturization of components of these measurement systems paves the way for opening up new markets. One example is the measurement of carbon dioxide ($CO_2$) concentrations in closed environments. The American Society of Heating, Refrigerating, and Air-Conditioning Engineers (ASHRAE) provided some insight into the role of demand controlled ventilation for buildings.

Figure 1A:
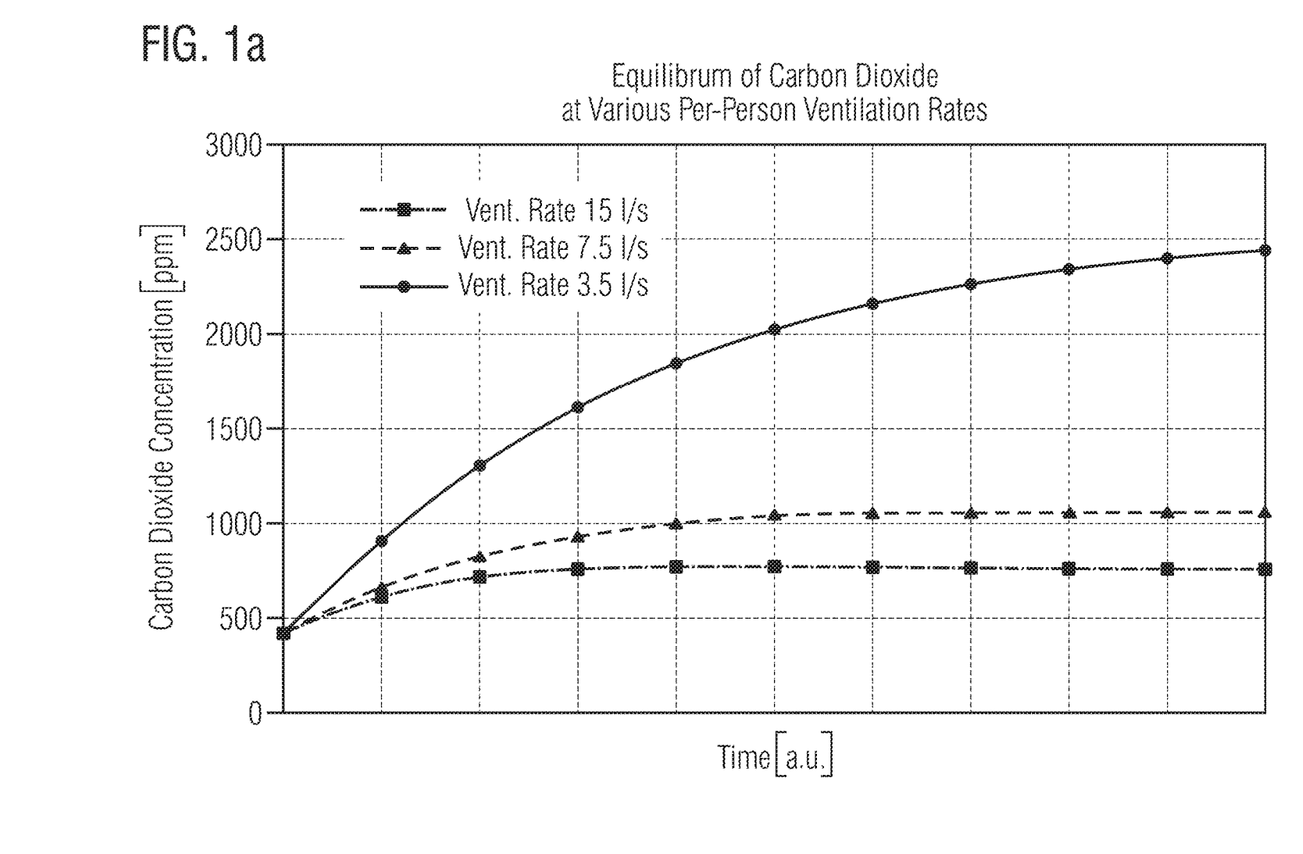
FIG. 1a illustrates a carbon dioxide concentration in a ventilated room as a function of time, with a ventilation rate as a parameter.
Figure 1B:
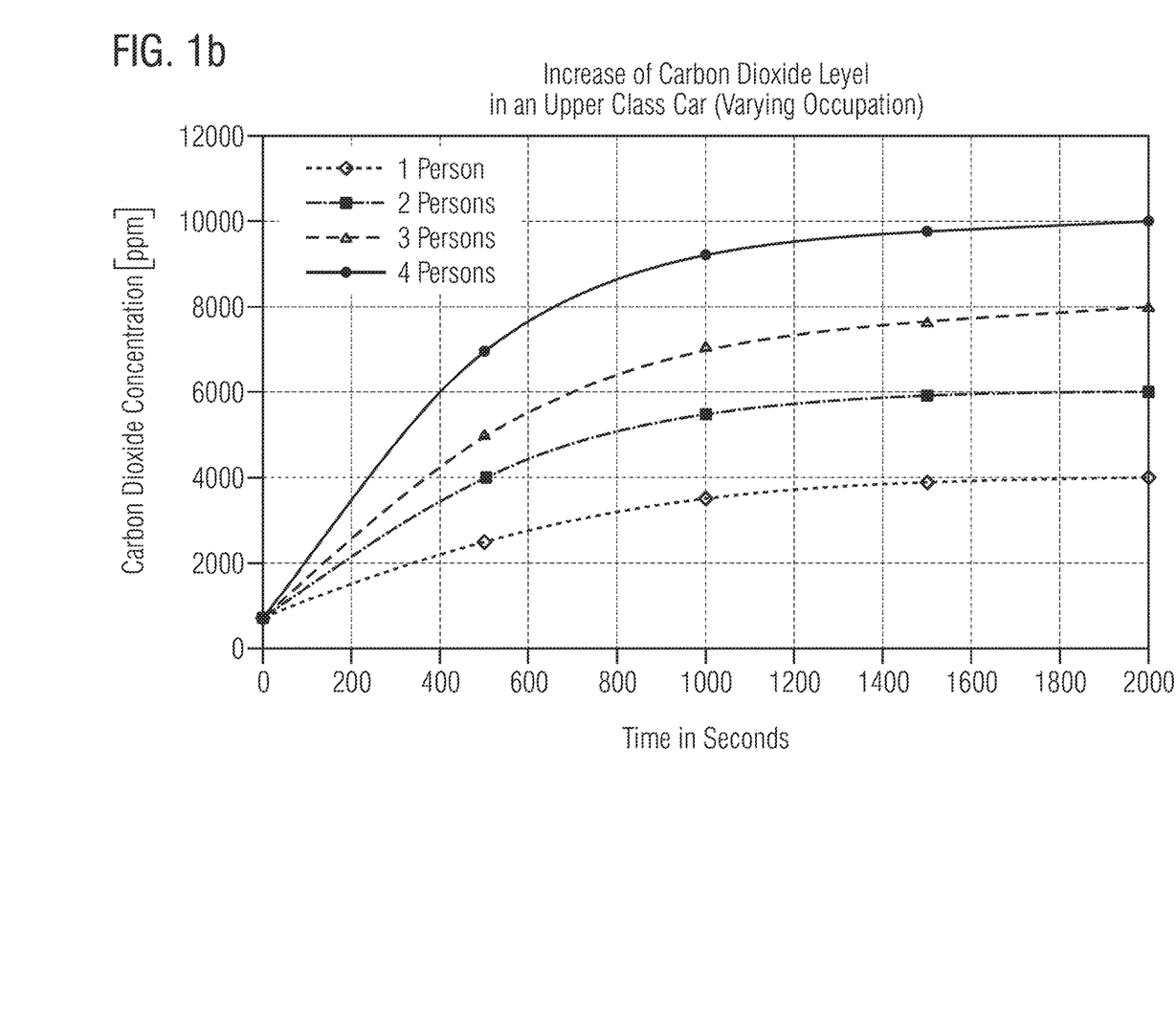
FIG. 1b illustrates a carbon dioxide concentration in an upper class car with stopped ventilation as a function of time, with a number of occupants as a parameter.

FIG. 1a and FIG. 1b illustrate the concentration of $CO_2$ in cars and buildings as a function of time (ventilation rate, number of occupants as parameters). FIG. 1a shows an example $CO_2$ concentration in a ventilated room as a function of time, with ventilation rate as a parameter. FIG. 1b depicts an example $CO_2$ concentration in an upper class car with stopped ventilation as a function of time, with a number of occupants as a parameter.

Acceptable $CO_2$ levels are in the range of 600 ppm (parts per million), complaints of stiffness and odors occur at 600 to 1000 ppm, general drowsiness is associated with 1000-2500 ppm. For the example of $CO_2$ concentration in cars, ventilation becomes a matter of safety. On the other hand, fuel efficiency is one of the driving factors in car automation. A reduction of fuel consumption at a level of up to 0.9 l/100 km have been estimated when a sensor-controlled ventilation by demand is used instead of conventional ventilation setups.

Heating at residential and public buildings is one major contributing factor of $CO_2$ emission in countries in temperate zones. In Germany, for example, the associated consumption of energy is currently roughly 7000 kWh per person and annum. This correlates to a $CO_2$ emission of approximately 3.5 tons (assuming oil or natural gasoline as predominant energy sources). Although heating of buildings is only a third of the overall energy consumption in Germany, the $CO_2$ emission for heating of buildings is already well above the level of 2 tons per person and annum that is acceptable concerning global warming. The reduction of efforts for heating of buildings is intimately connected with a gas-tight construction and demand controlled ventilation as a basis for efficient heat insulation.

The above illustrated facts show the need of sensor-controlled air quality management, for example. Two sensor approaches may be regarded as promising candidates for widespread usage in buildings: Non-dispersive infrared (NDIR) sensing systems and photo-acoustic sensors. Although both systems show sufficient resolution and key parameters, some major disadvantages are still unsolved—first of all sensor dimensions and costs.

A broad range of sensing principles for fluid or gas detection has been investigated in the past decades. For example, infrared spectroscopy may be performed using radiation in the infrared region of the electromagnetic spectrum (i.e., radiation having wavelengths of approximately 2-25 μm). Many modern days sensors, such as non-dispersive infrared (NDIR) $CO_2$ sensors, for example, use the infrared region of the electromagnetic spectrum to measure properties of fluid and/or gas samples. Such sensors generate IR radiation, which when brought into contact with the samples, reacts with the samples to cause a change (e.g., attenuation) in the IR radiation.

Figure 1C:
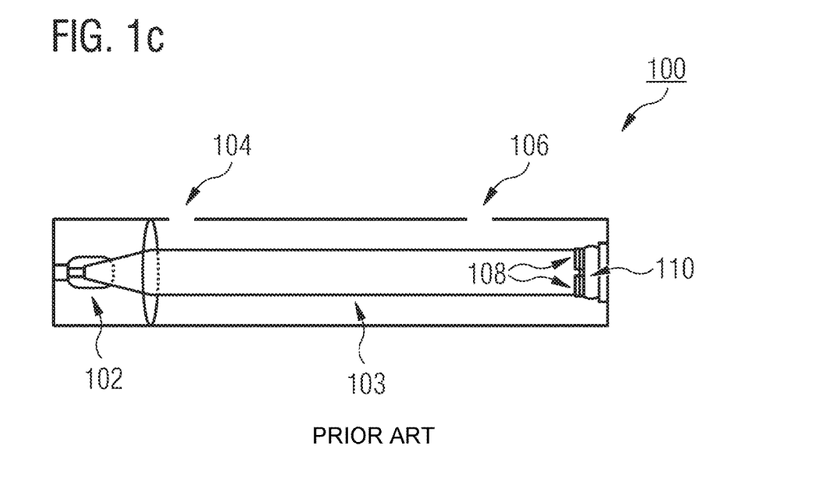
FIG. 1c shows a schematic diagram of a linear non-dispersive gas sensor with an optical path length in the range of centimeters.

FIG. 1c shows a schematic diagram of a conventional linear non-dispersive sensor 100. Sensor 100 includes a broadband infrared light source 102, a sample chamber 103, one or more light filters 108, and an infrared detector 110. The sample chamber 103 may comprise an inlet 104 and an outlet 106 for the sample, e.g., gas or fluid. Sensor 100 is non-dispersive in the sense of optical dispersion since infrared energy is allowed to pass through the atmospheric sample chamber 103 without deformation. Here, the optical path length of the conventional sensor 100 may be in the range of centimeters.

Sensor 100 measures changes in the IR radiation spectrum to determine properties of a sample in sample chamber 103. The measurement of characteristic absorption of the sample in the IR radiation spectrum, which represents a chemical fingerprint as particular substances, show stronger absorption at certain wavelengths being characteristic for the substance. This feature can be used by exposing the substance to broadband IR radiation and determining the absorption in the spectrum after the radiation has passed through or partly penetrated the sample.

One of the target research topics for NDIR sensors has been the optimization and reduction of optical path lengths needed for $CO_2$ detection in the 100 ppm range. Some investigations yielded single components of NDIR sensors as integrated parts of a silicon chip. Principally, all components have been demonstrated separately as silicon dies. However, the full advantage of silicon physical properties concerning infrared wave guiding and spectral filtering is rarely exploited in more than one component.

The reduction of the optical path length (millimeter and centimeter-range today) is one central task on the way to monolithically integrated (gas) sensors. One promising approach is the application of evanescent surface fields in waveguides of sub-wavelength diameters. To take full advantage of this concept, an efficient collimation and coupling of infrared light into the sub-wavelength fiber as well as an excellent thermal isolation of the light emitter is essential. Embodiments of the present disclosure address this issue.

Figure 2:
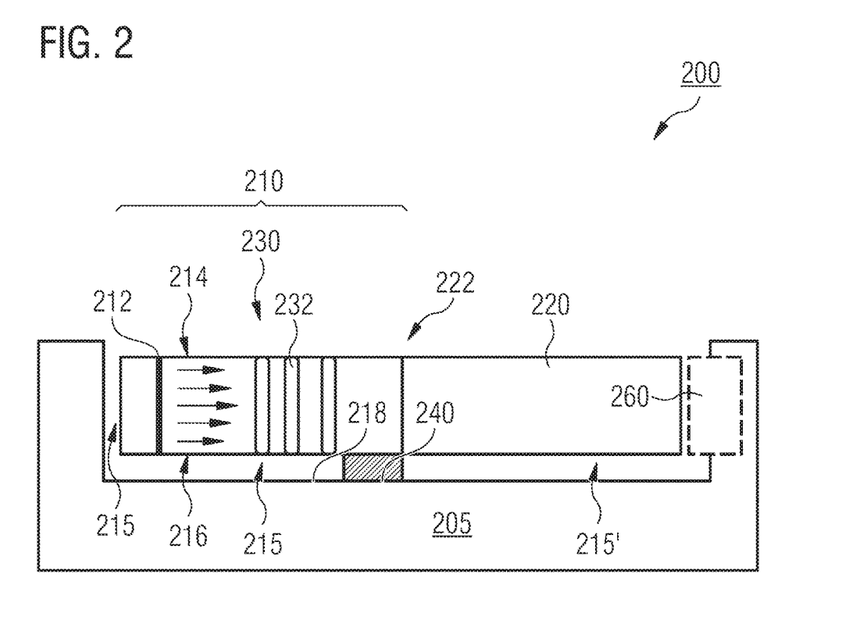
FIG. 2 illustrates a semiconductor-based integrated light emitting device according to one or more embodiments.

Turning now to FIG. 2, it is illustrated a schematic cross-sectional view of an integrated semiconductor light emitting device 200 according to one or more embodiments.

The integrated light emitting device 200 comprises a semiconductor substrate 205, such as a semiconductor wafer, for example. In various embodiments the semiconductor substrate 205 may be doped with an n-type or p-type dopant concentration or may not be doped. In other embodiments, the semiconductor substrate 205 may comprise an epitaxial layer. The semiconductor substrate 205 is made of semiconductor material, such as Silicon (Si) or Germanium (Ge), for example. Note that in principle also other semiconductor materials are possible as long as they provide a band gap between the valence band and the conduction band adequate for guiding light through the semiconductor material. The integrated light emitting device 200 further comprises a light emitting unit 210 integrated into the substrate's 205 semiconductor material. In other words, the light emitting unit 210 is formed or structured from and into semiconductor material of the semiconductor substrate 205. That is, the light emitting unit 210 and the substrate 205 may be formed monolithically. Various embodiments of the integrated light emitting device 200 are characterized in that at least one cavity 215 is formed into the semiconductor material between the substrate 205 and the light emitting unit 210. The cavity 215 separates the semiconductor based light emitting unit 210 from the remaining semiconductor substrate 205, thereby providing for thermal isolation between the light emitting unit 210 and the semiconductor substrate 205. For optimum thermal isolation the cavity 215 may be evacuated. The light emitting unit 210 above lower or bottom portions of the cavity 215 may be provided in a so-called Silicon-On-Nothing (SON) sheet layer. Consequently, the part of the cavity 215 below the light emitting unit 210 may be a SON cavity.

As illustrated in FIG. 2, the semiconductor body of the light emitting unit 210 may comprise an electrically conductive filament structure 212 as light source—similar to the filament of a bulb. Other light source implementations, such as electrically conductive plates or Light-Emitting Diodes (LEDs), for example, are also conceivable. However, forming the filament structure may be synergistically combined with forming other similar structures in the semiconductor device 200, such as trenches for optical filters, transistors or capacitors, for example. The electrically conductive filament structure 212 may be formed in the semiconductor body of the light emitting unit 210, for example, by using conventional deep trench etching processing technology. A structure with appropriate extension of a few microns to tens of microns may be etched in the light emitting unit's 210 semiconductor body and then be filled with electrically conductive material to obtain the conductive filament. Some examples of appropriate electrically conductive material for the filament 212 include tungsten, polycrystalline, crystalline, or amorphous semiconductor material. Some embodiments use a portion of the SON silicon layer as the emitting element. In this case, a trench structure is surrounding the said portion, leaving out only small fixtures between the emitting unit and the surrounding material.

In the example of FIG. 2, the electrically conductive filament structure 212 extends vertically from an upper surface 214 of the light emitting unit's 210 semiconductor body to a lower surface 216 of the light emitting unit's semiconductor body. That is, electrically conductive filament structure 212 extends perpendicular to a direction of light emitted from the light emitting unit 210. Respective electric supply terminals (not shown) may be provided to the upper and lower ends of the electrically conductive filament structure 212. In this way, the electrically conductive filament structure 212 may be configured to radiate (IR) light when an adequate supply voltage of below 1V to 20V is applied to the supply terminals.

Note that the at least one cavity 215 extends between the lower surface 216 of the light emitting unit 210 and an upper surface 218 of the semiconductor substrate 205. The lower surface 216 and the upper surface 218 face each other. The at least one cavity 215 provides thermal isolation between the light emitting unit 210 and the semiconductor substrate 205. As indicated in FIG. 2, the isolating cavity 215 may substantially surround the whole semiconductor body of the light emitting unit 210 to thermally isolate the light emitting unit 210 from the remaining semiconductor substrate 205 from which the light emitting unit 210 has been formed. That is to say, the cavity 215 may not only laterally separate the semiconductor body of the light emitting unit 210 and the substrate 205, but also vertically.

In order to mount or fix the light emitting unit 210 in the cavity 215, the integrated light emitting device 200 may comprise one or more support or fixation structures 240 deposited between the substrate 205 and the light emitting unit 210. The support or fixation structures 240 are configured to mount the light emitting unit 210 in the cavity 215. Here, the support structures 240 are configured as webs. In some embodiments, the one or more support structures 240 may comprise an insulating material, for example, an oxide of the semiconductor material, such as, for example, silicon dioxide ($SiO_2$). Note that the $SiO_2$ fixation 240 has a much smaller thermal conductivity compared to the Si of light emitting unit 210. Thermal isolation between light emitting unit 210 and substrate can hence be maintained. In this context the skilled person will appreciate that the support or fixation structures 240 should be dimensioned possibly small for possibly maximizing thermal isolation. The support structures 240 may be obtained by selective structuring/oxidization of the semiconductor substrate 205, for example.

As indicated by FIG. 2, the integrated light emitting device 200 may further comprise an optional waveguide 220 coupled to a light outlet 222 of the light emitting unit 210. The waveguide 220 may be configured to provide an interaction between light emitted from the light emitting unit 210 and guided by the waveguide 220 and a measurement medium (e.g. gas, fluid) surrounding the waveguide 220. The conveyed light forms an evanescent field that extends outward from the waveguide 220 to interact with a sample, e.g. a gas or a fluid, positioned in portions of the evanescent field. As the evanescent field interacts with the measurement medium the radiation guided by the waveguide 220 is attenuated according to one or more characteristics of the measurement medium (e.g., in particular, the radiation is absorbed in a wavelength region corresponding to the wavelength of the guided wave or waves). An optional light or radiation detector 260 may then be configured to receive the attenuated IR radiation and to determine the one or more characteristics of the sample from the attenuated IR radiation. The radiation detector 260 may include a Complementary Metal-Oxide-Semiconductor (CMOS) based infrared photodetector, for example. In some embodiments, the optional radiation detector 260 may comprise a radiation detector integrated into the semiconductor substrate 205, while in other embodiments the radiation detector 260 may comprise an external radiation detector.

Some embodiments make use of evanescent surface fields and a phenomenon called "frustrated total (internal) reflection". Total internal reflection occurs at the boundary of two dielectric media, e.g., between waveguide 220 and measurement medium surrounding the waveguide 220, if a light wave propagates from an optically denser medium refractive index $n_1$ into one of lower density refractive index $n_2$, and the angle of incidence exceeds the critical angle, given by $\arcsin(n_2/n_1)$. However, even if the angle of incidence is larger than the critical angle, the electric field penetrates into the adjacent medium in the form of an evanescent wave. The penetration depth is in the order of a wavelength, and can be measured by "frustrating" the reflection by adding an optically dense third medium at a distance on the order of a wavelength from the first medium, in which case the evanescent wave is coupled to the third medium and carries energy. The coupling strength falls off nearly exponentially as the distance between the first and third media is increased.

In the example embodiment of FIG. 2, the waveguide 220 and the light emitting unit 210 are integrally or monolithically formed into the semiconductor material. That is to say, both a body of the light emitting unit 210 and the waveguide 220 may be formed out of one piece of the same semiconductor material provided by the semiconductor substrate 205. Hence, the waveguide 220 may be a silicon waveguide in some embodiments. This allows for particularly well light emission and guidance, minimizing losses. The waveguide 220 may also be embedded in a cavity 215'. At least parts of cavity 215' may be formed by SON process technology. The cavity 215' may provide for thermal isolation between the waveguide 220 and the semiconductor substrate 205 as well as a measurement chamber for interaction between guided light and a measurement medium surrounding the waveguide 220. The skilled person having benefit from the present disclosure will appreciate that a separate arrangement of light emitting unit 210 and waveguide is also well possible.

Optionally, the light emitting unit 210 may also comprise a filter portion 230 formed in the semiconductor body of the light emitting unit 210. The filter portion 230 may be positioned between the broadband infrared light source 212 and the light emitting unit's light outlet 222 to filter the broadband infrared spectrum radiated by light source 212 in a manner that provides for a narrowband infrared radiation that is to be conveyed by the waveguide 220. In some embodiments, the filter portion 230 comprises one or more substantially parallel trenches 232 vertically extending into the light emitting unit's 210 semiconductor material. Other optical filter implementation, such as photonic crystals, for example, are also conceivable. However, forming the trenches may be synergistically combined with forming other structures in the semiconductor device 200, such as transistors or capacitors, for example. The widths of the respective trenches may be adapted to provide a pass band of the filter portion 230 in the spectral infrared region. The person having benefit from the present disclosure will appreciate that the same trench etching process steps may be used to form one or more vertical holes for the electrically conductive filament structure 212 and the trenches 232 of the filter portion 230.

Figure 3:
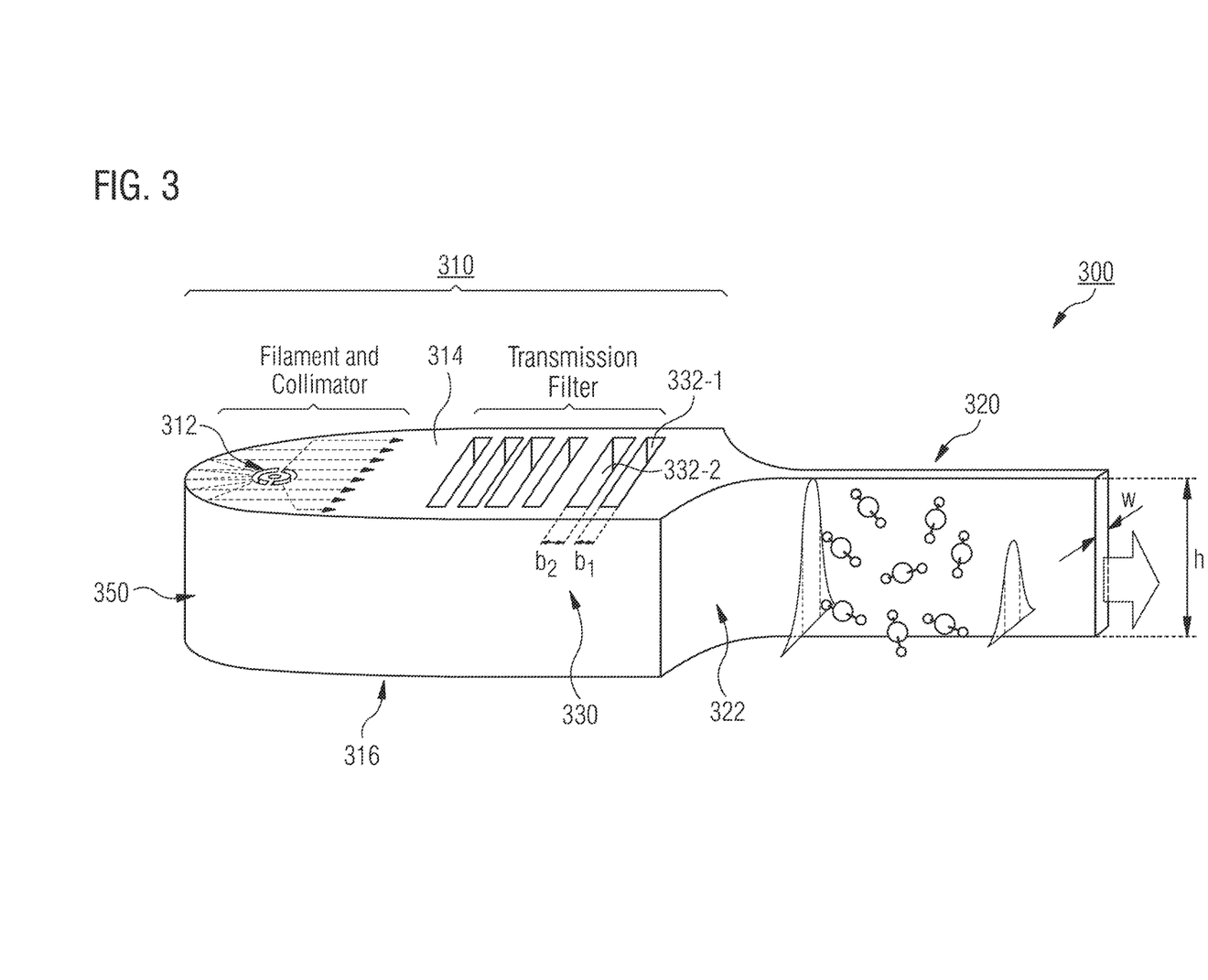
FIG. 3 shows a perspective view of a light emitting unit for IR spectral sensors according to one or more embodiments.

A perspective view of an example semiconductor component 300 of an integrated light emitting device is shown in FIG. 3. Note that the illustration of FIG. 3 does neither show any semiconductor substrate nor any cavities between the semiconductor substrate and the semiconductor component 300.

The illustrated semiconductor component 300 comprises a light emitting portion 310 and a waveguide portion 320. The light emitting portion 310 and the waveguide portion 320 are integrally formed from the semiconductor material of a SON sheet layer, i.e., a semiconductor layer covering a SON cavity. That is to say, in the shown example the light emitting portion 310 and the waveguide portion 320 constitute a single piece of semiconductor material. An IR signal may thus be directly coupled from the light emitting portion 310 to the waveguide portion 320. It may be advantageous to use sub-wavelength dimensions for width w and/or height h of the wave guide 320. For an example wavelength of 4.3 µm the width w may be about 2 µm, for example. As mentioned earlier, this may reduce the absorption length needed by several orders of magnitude. In the illustrated example, a vertical height h of the waveguide portion 320 is larger than a lateral width w of the waveguide portion 320. This may be beneficial for manufacturing purposes. For the mentioned effect of "frustrated total (internal) reflection" w and/or h should be smaller than the light's wavelength. A doping in the waveguide 320 should not be too large. In some examples, the concentration of n- or p-type dopants should be smaller than $10^{15}/cm^3$ Since a lateral width of the light emitting portion 310 is larger than the lateral width w of the waveguide portion 320, a transition 322 from the light emitting portion 310 to the waveguide portion 320 is formed trumpet-like in the embodiment of FIG. 3. Note, however, that other geometries of light emitting portion 310 and the waveguide portion 320 are also possible.

As has already been explained with reference to FIG. 2, the light emitting portion 310 of FIG. 3 comprises a broadband IR light source 312 and a filter structure 330 formed into the semiconductor material between the light source 312 and the waveguide portion 320. The filter structure 330 comprises a plurality of trenches 332 formed into the semiconductor material of the light emitting portion 310. The plurality of trenches 332 may be evacuated, respectively. Also, different trenches 332-1, 332-2 may have different respective thicknesses $b_1$, $b_2$. The respective dimensions of the different trenches is relevant for the pass-band of the optical filter structure 330. An example for an infrared filter stack has been calculated using silicon and vacuum for alternated optical layers. The thicknesses of single layers are well in the ballpark of processing capabilities of state-of-the-art deep trench etching. The simulated transmission spectrum for a silicon/vacuum layer stack as illustrated in FIG. 3 is shown in FIG. 4.

Figure 4:
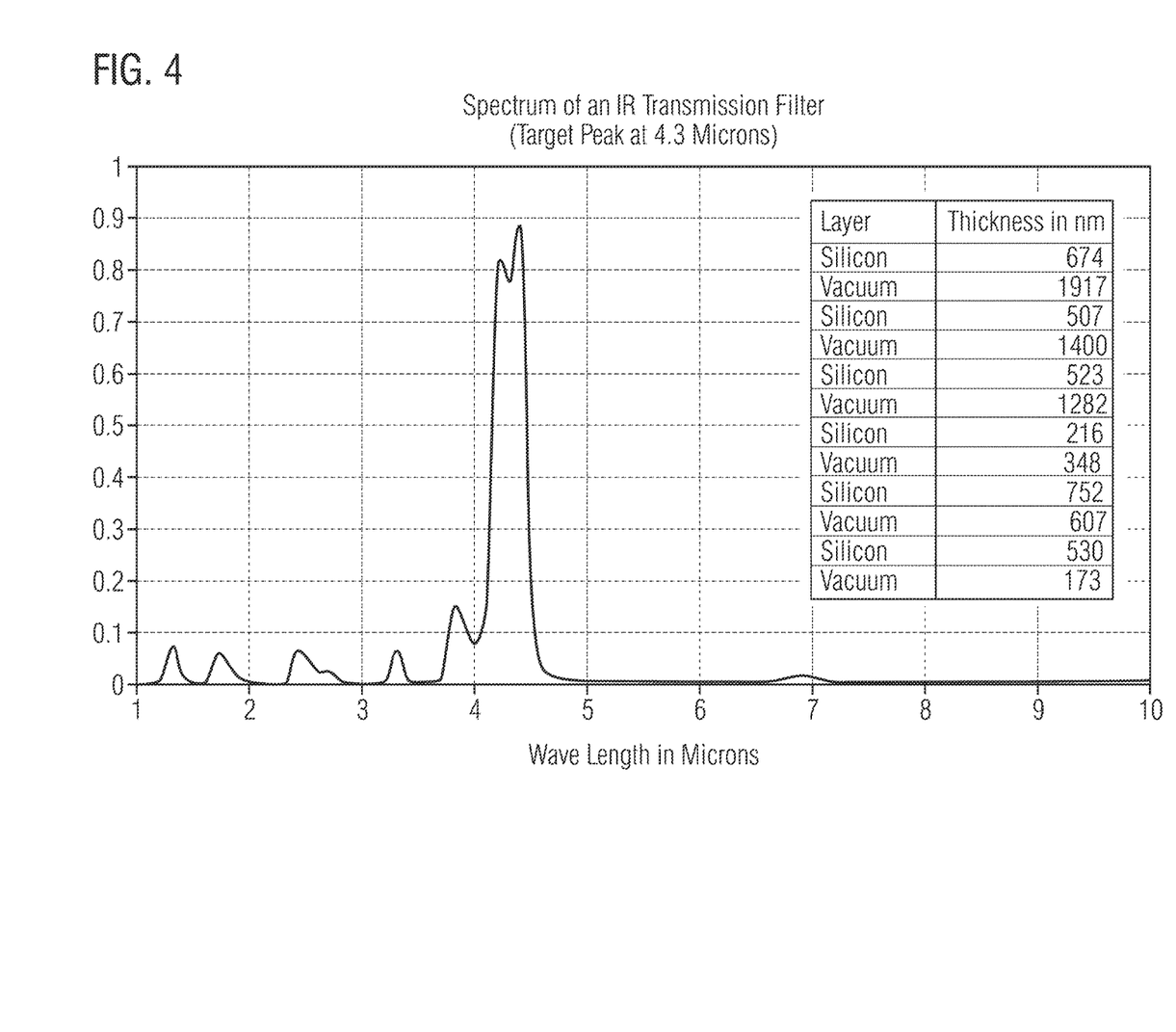
FIG. 4 shows a simulated transmission spectrum for a silicon/vacuum layer stack as illustrated in FIG. 3.

As can be seen from FIG. 4, providing the filter structure 330 with a stack silicon/vacuum layers with the respective illustrated thicknesses leads to a narrow pass band around an IR wavelength of approximately 4.3 µm.

Turning back to FIG. 3, the light emitting portion 310 further comprises a beam shaping portion 350 at the end opposing the waveguide portion 320. The beam shaping portion 350 is configured to collimate light radiated from the light source 312. In the shown example, the beam shaping portion 350 comprises a light-reflecting curved or parabolic edge of the light emitting unit's semiconductor material. Preferably, the light source 312, e.g. the electrically conductive filament, substantially extends through a focus of the rounded or parabolic edge. Here, the electrically conductive filament 312 substantially corresponds to a focal line extending from a top surface 314 to a bottom surface of the parabolic beam shaping portion 350. The skilled person will appreciate that also lens structures could be implemented as optical collimator. Also in this case the light source would be positioned in the focus of the lens.

Figure 5:
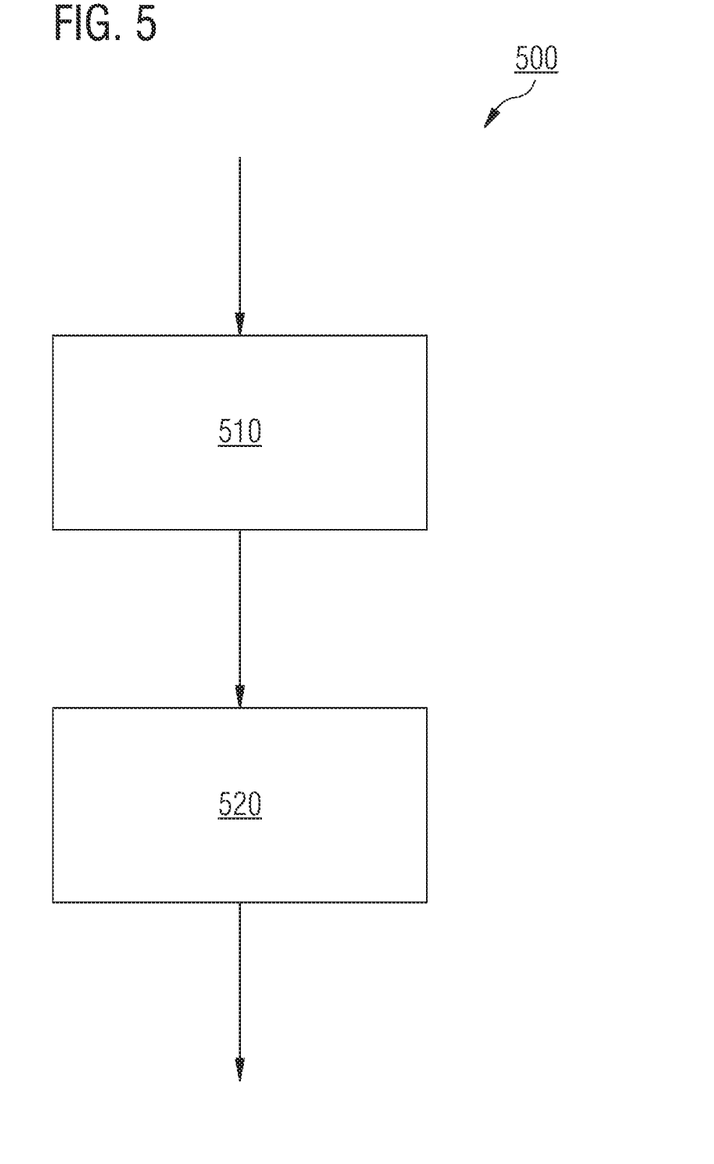
FIG. 5 illustrates a high-level flowchart of a method for manufacturing a semiconductor-based integrated light emitting device according to one or more embodiments.

As schematically shown by FIG. 5, embodiments also provide a method 500 for forming the integrated light emitting device 200.

Method 500 includes integrating 510 the light emitting portion 210, 310 into the semiconductor material of the semiconductor substrate 205, and forming 520 the at least one cavity 215 into the semiconductor material between the semiconductor substrate 205 and the light emitting portion 210, 310. As will be appreciated by the skilled person having benefit from the present disclosure, integrating 510 the light emitting portion 210, 310 and forming 520 the at least one cavity 215 are closely interrelated. The light emitting portion 210, 310 is formed into the semiconductor substrate 205 by forming 520 the at least one cavity 215 below and/or beside and/or above the light emitting portion 210, 310, and vice versa. That is to say, an order of acts 510 and 520 may also be reversed.

Some embodiments use a so-called Silicon-On-Nothing (SON) processing sequence to form the at least one cavity 215 and/or to provide further basic structural elements of integrated light emitting device 200. In other words, the at least one cavity 215 between the substrate 205 and the light emitting unit 210 may be provided by applying a SON processing sequence, an example of which will be explained in more detail below.

After forming a SON sheet layer, in which light emitting portion 210, 310 and waveguide portion 220, 320 may be structured later, a deep trench etch may define filament 212, 312, transmission filter 230, 330 and emitting/absorption portions. Intermediate oxidation processes may transform silicon fixations 240 between substrate 205 and light emitting unit 210, 310 to a silicon oxide layer. In this way, the thermal power conduction between emitter and substrate 205 may be minimized.

Beside the use of sacrificial layers below the SON sheet layer for the fabrication of a silicon on nothing (SON) structure, a further practical method for obtaining SON structures with a desired size and shape may use the so-called Empty-Space-in-Silicon (ESS) formation technique. It has been shown that a SON structure can be precisely controlled by the initial shape and layout of trenches. The size of ESS is determined by the size of the initial trench(es). The desired shapes of ESS, such as spherical, pipe-shaped and plate-shaped, can be fabricated by changing the arrangement of the initial trenches. Some examples of SON processing make use of the self-organizing recrystallization caused by silicon surface migration. The initial trench shape patterned on the silicon substrate may be regarded as the most important factor to fabricate a SON structure. The trench structure transforms so as to minimize the surface energy, when it is annealed in a deoxidizing ambient, such as hydrogen.

Trench transformation by surface migration results in the Empty-Space-in-Silicon (ESS). The SON structure can be made of SON sheet layer over ESS by this means. Typical examples of ESS formation, whose shapes are spherical, pipe-shaped and plate-shaped, are schematically illustrated in FIG. 6.

Figure 6A:
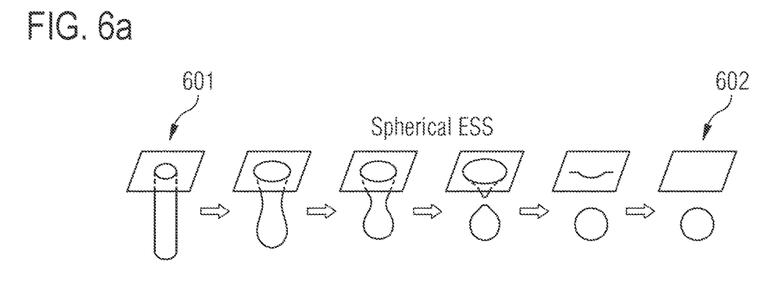
FIGS. 6a-6c show various principles of forming Silicon-On-Nothing (SON) cavities.
Figure 6B:
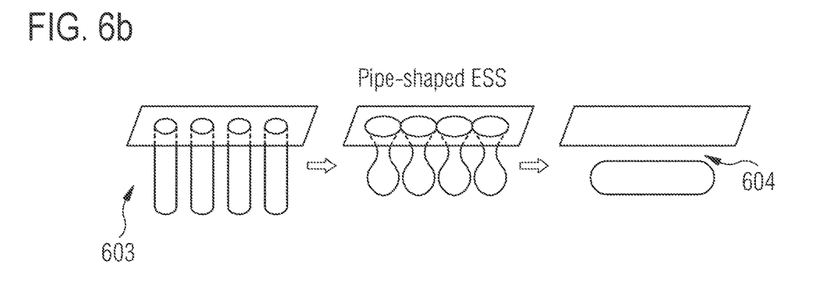
Figure 6C:
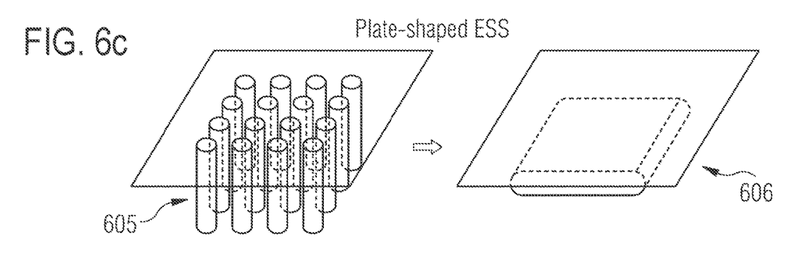

An isolated deep trench 601 may be transformed to a spherical ESS 602, see FIG. 6a. Formation of the spherical ESS begins at the top and bottom corners of the deep trench, because the radius of curvature of these regions is the smallest. This result indicates that the diameter of the spherical ESS becomes larger than that of the initial trench. Thus, trenches 603 closely arranged in a row are transformed to the pipe-shaped ESS 604, due to the combination of the grown spherical ESS at the bottom of each trench, see FIG. 6b. A plate-shaped ESS 606 can also be fabricated by developing this technique. By arranging the trenches in a lattice 605, the spherical ESSs at the bottom of all trenches are combined, and they are transformed to a large, thin plate-shaped ESS 606, see FIG. 6c.

Figure 7:
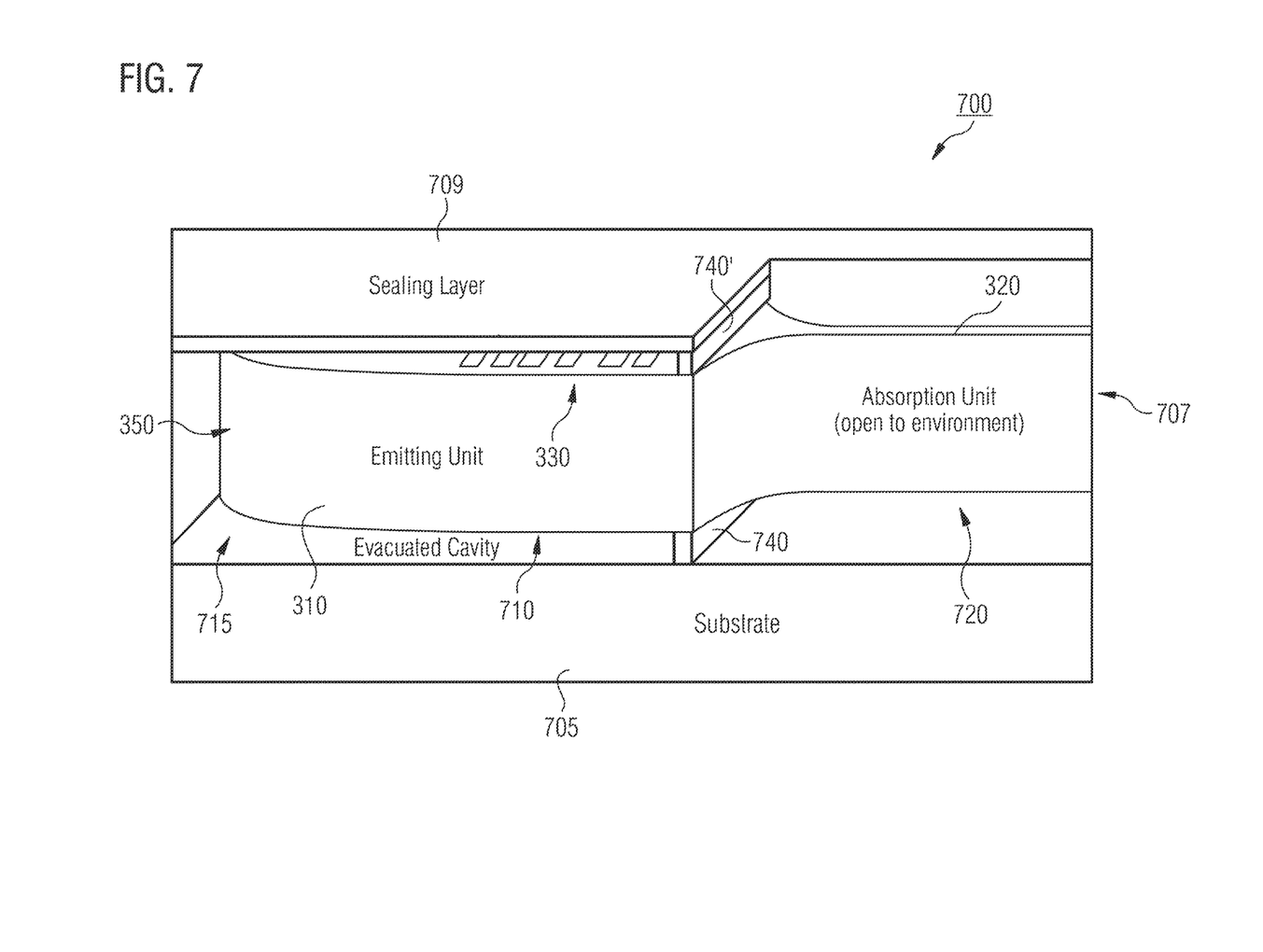
FIG. 7 illustrates a final structure of a semiconductor-based integrated light emitting device after sealing and evacuation.

Turning now to FIG. 7, it is illustrated a schematic perspective view of an integrated semiconductor light emitting device 700 according to one or more further embodiments. For the sake of brevity a detailed description of like or similar elements that have been described before will be omitted.

The integrated semiconductor device 700 comprises a semiconductor substrate 705. In a SON sheet layer 707 above the semiconductor substrate 705 the integrated semiconductor device 700 comprises a light emitting unit 310 integrally formed with a waveguide 320 in the SON sheet layer 707. Light emitting unit 310 and waveguide 320 have been explained in detail with reference to FIG. 3. Above the SON sheet layer 707 the integrated semiconductor device 700 also comprises a sealing layer 709. The sealing layer 709 may comprise various sealing materials, such as thermoplastic, elastomeric or metallic materials, for example. Here, silicon oxide, silicon nitride or polysilicon layers are appropriate candidates as well. $SiO_2$ fixations 740 and 740' fix light emitting unit 310 and waveguide 320 in between the semiconductor substrate 705 and the sealing layer 709. At the same time the fixations 740 and 740' seal the light emitting unit 310 off a measurement environment. In other words, the light emitting unit 310 is arranged in a portion of the semiconductor device 700 sealed off an outer environment. Boundaries or sidewalls of the sealed portion are formed by the substrate 705 (bottom), the sealing layer 709 (top), and the $SiO_2$ fixations 740 and 740'. The light emitting unit 310 in the sealed portion is surrounded by or embedded in an evacuated cavity 715 for thermal isolation. As can be seen from the illustrative example of FIG. 7, the light emitting unit 310 may be surrounded by the evacuated cavity 715 from below, above, left, before, and behind the light emitting unit 310. Only the right side of light emitting unit 310 with the sideways optical signal outlet may be supported by the $SiO_2$ fixations 740 and 740' and adjoin the measurement environment. At least the cavity portion below the light emitting unit 310 may be formed by SON processing. The skilled person will appreciate that other geometries may also be well suited for sufficient thermal isolation between semiconductor substrate 705 and light emitting unit 310.

The semiconductor based waveguide 320 extends from the light emitting unit 310 in the sealed portion 710 to a portion 720 of the semiconductor device 700 which is open to the measurement environment. This open portion 720 may also be referred to as absorption portion or unit. The waveguide 320 extending through the open absorption portion 720 is configured to provide interaction between guided light and a measurement medium, e.g., a gas or a liquid, surrounding the waveguide 320 in the absorption portion. For example, in order to provide inlets and/or outlets the sealing layer 709 may be at least partially open above the waveguide 320 in the absorption portion 720. A length of the waveguide 320, i.e., the optical path length, may be in the range of 10 μm to several 100 μm.

Figure 8:
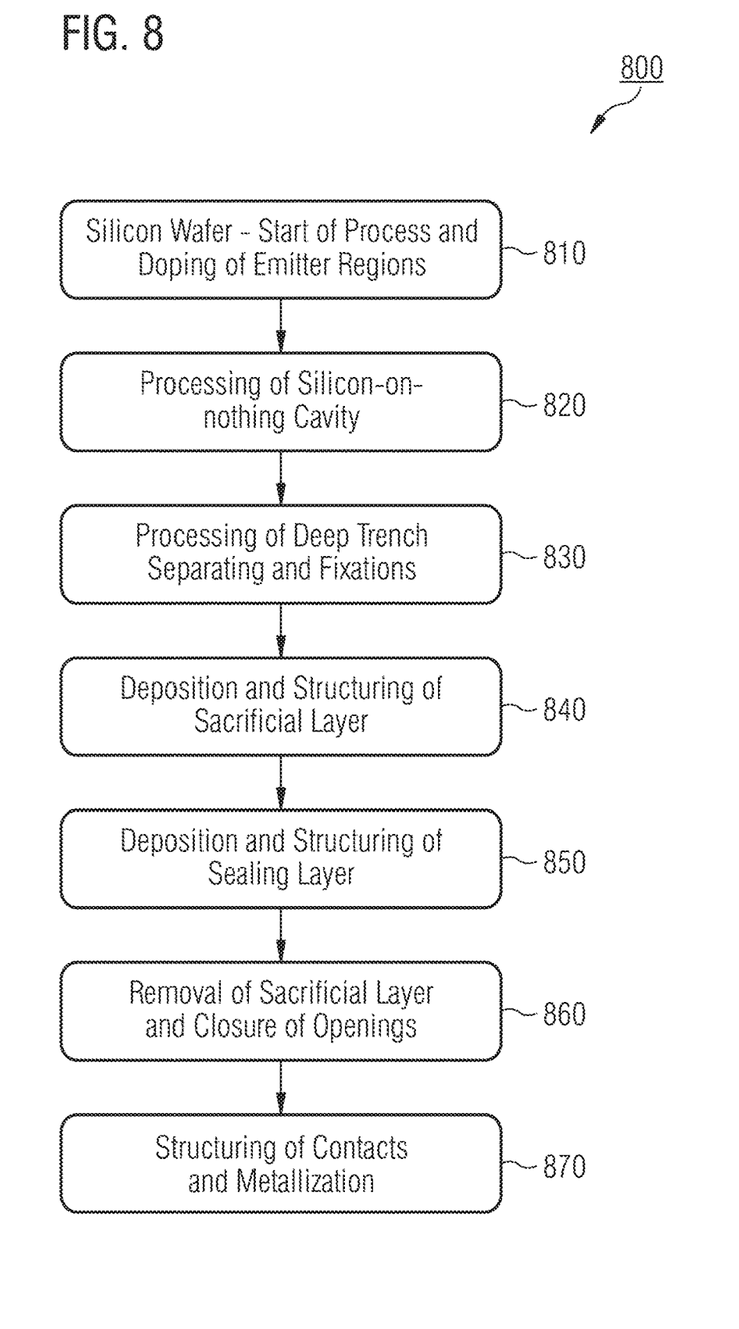
FIG. 8 shows a flowchart of a method for manufacturing the semiconductor-based integrated light emitting device of FIG. 7.

An embodiment of integrated semiconductor device 700 may be manufactured by using the example method 800 illustrated in FIG. 8. It will be appreciated that while method 800 is illustrated and described below as a series of acts or events, the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the disclosure herein. Also, one or more of the acts depicted herein may be carried out in one or more separate acts and/or phases.

Method 800 starts with the provision and appropriate doping 810 of a Si wafer. For example, certain regions of the later light emitting unit 310 may be doped. In a further act 820 the SON-cavities 715, 715' may be processed. This may include etching of sacrificial layers and/or ESS formation as explained above, for example. In a subsequent act 830 the light emitting and waveguide portions 310, 320 above the SON-cavities 715, 715' may be formed in the semiconductor substrate by further deep trench etching acts. To obtain the portions of the cavities 715, 715' above the light emitting and waveguide portions 310, 320 one or more further sacrificial layers may be deposited and structured above the SON sheet layer 707 in an act 840. During this act the upper $SiO_2$ fixation 740' may be obtained. After that, in an act 850, sealing layer 709 may be deposited and structured above the SON sheet layer 707. In a further act 860, sacrificial layers may be removed by selective etching. Finally, metallization layers may be structured for electrical routing and/or contacts, see 870.

When combining the integrated light emitting devices 200, 700 with a light sensor or detector integrated on the same semiconductor substrate, an integrated sensor device may be provided. The integrated sensor device then comprises a semiconductor substrate, a light emitting unit formed into the semiconductor substrate, a light detecting unit formed into the semiconductor substrate, and a waveguide formed into the semiconductor substrate between the light emitting unit and the light detecting unit. The waveguide is formed in a portion of the semiconductor substrate open to an environment to provide interaction between guided light and a measurement medium surrounding the waveguide. The light emitting unit is formed in a portion of the semiconductor substrate sealed off the environment. Further, the light emitting unit in the sealed portion is at least partially surrounded by an evacuated cavity. The integrated sensor device may be used as NDIR $CO_2$ sensor, for example.

To summarize, some embodiments combine an integrated infrared emitter, a collimation unit and a spectral filter on a single silicon element. This element is thermally isolated from the surrounding material by evacuated cavities. Some embodiments provide an infrared emitting unit that may directly couple the signal into a fiber element for immediate interaction of IR signal and surrounding fluid. The usage of silicon as emitter and wave guide material may lead to a very compact integration of collimator and filter elements. A sideways main propagation of infrared signals allows simple ways of integration of optical elements. The usage of a combined silicon-on-nothing and sealing technique guarantees minimum thermal losses by providing an evacuated cavity surrounding the emitter element.

Various embodiments include:

Infrared emitting element with sideways signal outlet;

Element made from SON silicon with a filament that is surrounded by beam shaping elements and filters, in the same level inside the silicon construction;

Emitting unit that is surrounded by an evacuated cavity;

Emitting unit that couples the IR beam directly into a silicon wave guide in the same level inside the silicon construction;

Wave guide element formed by means of SON and deep trench etch processes, in one embodiment formed as a sub-wavelength waveguide (concerning width and/or height).

The above shown examples may be configured with parts omitted, such as an emitting unit without a filter system. Further on, other elements may be combined. One example would be a drain for unused spectral components attached to the emitting unit. Such a drain could be a filter system that has an inverted transmission functionality compared to the filter shown in FIG. 4. This second filter may be combined with the collimator at defined regions. The emitting filament may also be formed in a non-cylindrical way (e.g. as a plate).

The description and drawings merely illustrate the principles of the disclosure. It will thus be appreciated that those skilled in the art will be able to devise various arrangements that, although not explicitly described or shown herein, embody the principles of the disclosure and are included within its spirit and scope. Furthermore, all examples recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions. Moreover, all statements herein reciting principles, aspects, and embodiments of the disclosure, as well as specific examples thereof, are intended to encompass equivalents thereof.

Furthermore, the following claims are hereby incorporated into the detailed description, where each claim may stand on its own as a separate example embodiment. While each claim may stand on its own as a separate example embodiment, it is to be noted that—although a dependent claim may refer in the claims to a specific combination with one or more other claims—other example embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective acts of these methods.

Further, it is to be understood that the disclosure of multiple acts or functions disclosed in the specification or claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

What is claimed is:

1. An integrated light emitting device, comprising:
   a substrate of semiconductor material, wherein the substrate includes a main surface extending in a lateral direction;
   a light emitting unit integrated into the semiconductor material of the substrate, wherein the substrate and light emitting unit are monolithically formed from the semiconductor material, and wherein the light emitting unit is configured to emit a light beam directed in the lateral direction;
   at least one cavity formed into the semiconductor material between the substrate and the light emitting unit; and
   at least one insulating support structure coupled between the light emitting unit and the substrate,
   wherein the at least one cavity and the at least one insulating support structure are configured to insulate the light emitting unit and the substrate from each other.

2. The integrated light emitting device of claim 1, wherein the light emitting unit comprises an electrically conductive structure formed vertically in the semiconductor material as a light source, wherein the electrically conductive structure is configured to emit light when a supply voltage is applied to terminals of the electrically conductive structure.

3. The integrated light emitting device of claim 2, wherein the electrically conductive structure comprises crystalline, polycrystalline or amorphous semiconductor material.

4. The integrated light emitting device of claim 2, wherein the electrically conductive structure comprises an electrically conductive filament extending perpendicular to the lateral direction of the light beam emitted from the light emitting unit.

5. The integrated light emitting device of claim 2, wherein the light emitting unit further comprises a beam shaping portion extending in the lateral direction and configured to collimate light emitted from the electrically conductive structure.

6. The integrated light emitting device of claim 5, wherein the beam shaping portion comprises a light-reflecting curved or parabolic edge of a semiconductor material of the light emitting unit.

7. The integrated light emitting device of claim 6, wherein the electrically conductive structure substantially extends through a focus of the curved or parabolic edge.

8. The integrated light emitting device of claim 1, wherein the light emitting unit further comprises a filter portion formed in the semiconductor material.

9. The integrated light emitting device of claim 8, wherein the filter portion is configured to have at least one pass band in a spectral infrared region.

10. The integrated light emitting device of claim 8, wherein the filter portion comprises one or more trenches formed into a semiconductor material of the light emitting unit.

11. The integrated light emitting device of claim 1, wherein the light emitting unit is arranged in a portion of the semiconductor material sealed off from an environment.

12. The integrated light emitting device of claim 11, wherein the light emitting unit in the sealed portion is at least partially surrounded by an evacuated cavity.

13. The integrated light emitting device of claim 1, further comprising:
    a sealing layer formed above the light emitting unit; and
    at least one cavity between the light emitting unit and the sealing layer.

14. The integrated light emitting device of claim 1, further comprising:
a waveguide coupled to a light outlet of the light emitting unit, wherein the waveguide is configured to provide interaction between guided light and a measurement medium surrounding the waveguide.

15. The integrated light emitting device of claim 14, wherein the waveguide and the light emitting unit are integrally formed into the semiconductor material, wherein the waveguide and light emitting unit are monolithically formed from the semiconductor material.

16. The integrated light emitting device of claim 14, wherein the waveguide is arranged in a portion of the semiconductor material open to an environment, and wherein the light emitting unit is arranged in a portion of the semiconductor material sealed off from the environment.

17. The integrated light emitting device of claim 14, wherein a width of the waveguide is smaller than a wavelength of light emitted by the electrically conductive structure.

18. An integrated sensor device, comprising:
a semiconductor substrate, wherein the semiconductor substrate includes a main surface extending in a lateral direction;
a light emitting unit formed into the semiconductor substrate, wherein the semiconductor substrate and light emitting unit are monolithically formed from a semiconductor material, and wherein the light emitting unit is configured to emit a light beam in the lateral direction;
at least one insulating support structure coupled between the light emitting unit and the semiconductor substrate;
a light detecting unit formed into the semiconductor substrate; and
a waveguide formed into the semiconductor substrate between the light emitting unit and the light detecting unit;
wherein the waveguide is formed in a portion of the semiconductor substrate open to an environment to provide interaction between guided light and a measurement medium surrounding the waveguide,
wherein the light emitting unit is formed in a portion of the semiconductor substrate sealed off from the environment, and
wherein the light emitting unit in the sealed portion is at least partially surrounded by an evacuated cavity such that the light emitting unit and the semiconductor substrate are insulated from each other.

19. A method for forming an integrated light emitting device, the method comprising:
integrating a light emitting unit into a semiconductor material of a semiconductor substrate, wherein the semiconductor substrate and the light emitting unit are monolithically formed from the semiconductor material;
depositing at least one insulating support structure on the semiconductor substrate such that the at least one insulating support structure is coupled between the light emitting unit and the semiconductor substrate; and
forming at least one cavity into the semiconductor material between the semiconductor substrate and the light emitting unit.

20. The method of claim 19, wherein forming the at least one cavity comprises using a Silicon-On-Nothing (SON) processing sequence.

* * * * *